United States Patent [19]

Boinet et al.

[11] 4,165,631

[45] Aug. 28, 1979

[54] INSTRUMENT FOR THE CONTINUOUS MEASUREMENT OF VISCOSITY, ESPECIALLY OF BITUMENS

[75] Inventors: Abel Boinet, Pau; Lucien Mondeil, Serres Morlaas; Jean-Louis Montay, Pau, all of France

[73] Assignee: Elf-Union, Paris, France

[21] Appl. No.: 901,092

[22] Filed: Apr. 28, 1978

[30] Foreign Application Priority Data

May 4, 1977 [FR] France .................................. 77 13526

[51] Int. Cl.² .......................................... G01N 11/00
[52] U.S. Cl. .......................................... 73/54; 73/59
[58] Field of Search ........................ 73/54, 59, 55, 56

[56] References Cited

U.S. PATENT DOCUMENTS

| 2,679,750 | 6/1954 | Brookfield | 73/59 |
| 2,837,913 | 6/1958 | Rich et al. | 73/59 |
| 3,116,631 | 1/1964 | Rosenthal | 73/56 |

FOREIGN PATENT DOCUMENTS 2252784 6/1975 France .................................. 73/59

Primary Examiner—Charles A. Ruehl
Assistant Examiner—Joseph W. Roskos

[57] ABSTRACT

The instrument comprises a viscometer for a product such as bitumen and a pump for transferring the product to a flat wall-type heat exchanger. A channel formed in the heat exchanger wall is brought to an adjustable temperature and the channel output is connected to the viscometer. A probe for measuring the temperature of the product is placed within the viscometer, the temperature being adjusted to an index value within a predetermined range by means of a regulator for varying the pump output and controlling the temperature of the heat-exchanger wall.

12 Claims, 3 Drawing Figures

INSTRUMENT FOR THE CONTINUOUS MEASUREMENT OF VISCOSITY, ESPECIALLY OF BITUMENS

This invention relates to an instrument for the continuous measurement of the viscosity of bitumens or like high-viscosity products. The invention finds an application whenever it proves necessary to test the quality of a bitumen, for example at the time of loading of trucks (lorries) or at the time of manufacture in mixers.

Instruments for measuring the viscosity of a product can have recourse to a wide range of different methods, depending on the nature of the product and the value of its viscosity. If the product is in a fairly fluid state, it is possible to adopt the method which consists in passing the product through a capillary tube and in measuring the pressure drop through the tube. If the product is in a highly viscous state, recourse can in that case be had to another method which consists in forcing the product through a diaphragm and measuring the pressure obtained upstream of said diaphragm. In the case of intermediate products and especially hot bitumens or heavy oils having a viscosity of the order of 1 to 10 poises, preference may be given to the so-called Brookfield method summarized below.

In this method, a cylinder is immersed in the product whose viscosity is to be measured and is driven in rotation at constant speed. A measurement is then taken of the reaction torque produced by tangential friction of the cylinder in the bitumen, the value of torque being proportional to the viscosity to be measured. As a general rule, the value of this viscosity is converted to an electrical signal which is represented in analog form on a display device. The viscometer which is designated by the trade name "Contraves" falls in this class of instrument.

These measuring instruments suffer from a drawback in that they are not designed to control the temperature of the fluid to be measured. They therefore give a value which is no doubt correct but which is dependent on the temperature to a considerable extent. It is not possible under these conditions to compare the qualities of two fluids whenever they are at different temperatures; neither is it possible to check the quality of a predetermined bitumen with respect to standards which have been established for a temperature of 25° C. in the majority of cases. Testing under these conditions is non-continuous and performed too late to permit of any change in quality.

It is known in particular that the majority of international quality standards adopted in this field relate to a so-called measurement of penetrability which has to be taken at 25° C. Correlations which have been made show that this indication of penetrability could be related to a measurement of viscosity at 150° C. on condition that the temperature is stabilized at ±0.1° C. and that the measurement of viscosity is performed to within 1%. The narrowness of this margin clearly shows the degree of accuracy to be observed in the determination of this parameter if the measurement is to have any real significance. It also provides an indication of the difficulties which have to be overcome in order to bring within this range the temperature of a product such as bitumen which is not only viscous but which also has low thermal conductivity.

If it is added that bitumen can very easily be at a temperature which is far removed from 150° C. and can be of the order of 130° 1 C. or 180° C., for example, it becomes clear that a conventional viscometer is insufficient.

The precise aim of the present invention is to provide an instrument which is capable of measuring viscosity and which is capable at the same time of performing the function of key importance mentioned in the foregoing, namely that of accurate measurement of the temperature of the product to be measured.

In more exact terms, this invention is directed to an instrument for continuous measurement of viscosity of bitumens in particular, of the type comprising a viscometer adapted to the product whose viscosity is to be measured, and an entraining pump for receiving and transferring said product to a heat exchanger constituted by a wall in which is formed a channel for the circulation of said product, said wall being brought to an adjustable temperature by suitable means, the output of said channel being connected to a viscometer. The instrument is distinguished by the fact that the output of the entraining pump can be varied at will and that it comprises in addition:

a probe for measuring the temperature of the product, said probe being placed within the viscometer at the point of measurement of viscosity, and regulating means for adjusting said temperature to an index value comprised between a lower-limit temperature $T_1$ and an upper-limit temperature $T_2$, said regulating means being adapted to produce action on the output of the pump and on the means for controlling the temperature of the heat-exchanger wall.

Moreover, the invention provides an improvement over instruments of the prior art in that means are provided for interrupting the recording of the result of the measurement when the temperature of the product is not within the desired temperature range, that is to say in practice and in the case of bitumen within the range of 150° C.±0.1° C. The recording means are advantageously of the digital type and not of the analog type as in the prior art.

The instrument in accordance with the present invention is provided with safety means which are based on measurements of temperature and pressure and which are intended to protect the elements of the viscometer, of the heat exchanger or of the instrument. This applies in particular to the viscometer bearings on which the cylinder driving shaft are rotatably mounted, said bearings being usually made of materials such as sapphire which are subject to rapid deterioration under the action of abrupt temperature variations.

In addition to the advantages mentioned in the foregoing, the instrument in accordance with the invention affords the advantage of rapid replenishment of the product. This advantage is not negligible if it is borne in mind that the quality of a bitumen is not necessarily the same throughout an entire charge, with the result that it consequently proves desirable to carry out a number of measurements at very close intervals during any one charging operation. Approximately ten measurements for one charging operation which takes about twenty minutes appears to be reasonable. In the case of the Contraves viscometers of the prior art, the measuring cell in which the cylinder rotates has a dead volume of the order of one half liter, which is prohibitive for the rapid renewal of the product to be measured. This dead volume is reduced to approximately ⅛ of a liter in the present invention, thus permitting more rapid replenishment of the bitumen within the measuring cell.

The distinctive features and advantages of the present invention will in any case become more readily apparent from the following description of one exemplified embodiment which is given by way of explanation and not in any limiting sense, reference being made to the accompanying drawings, wherein.

Figure 1:
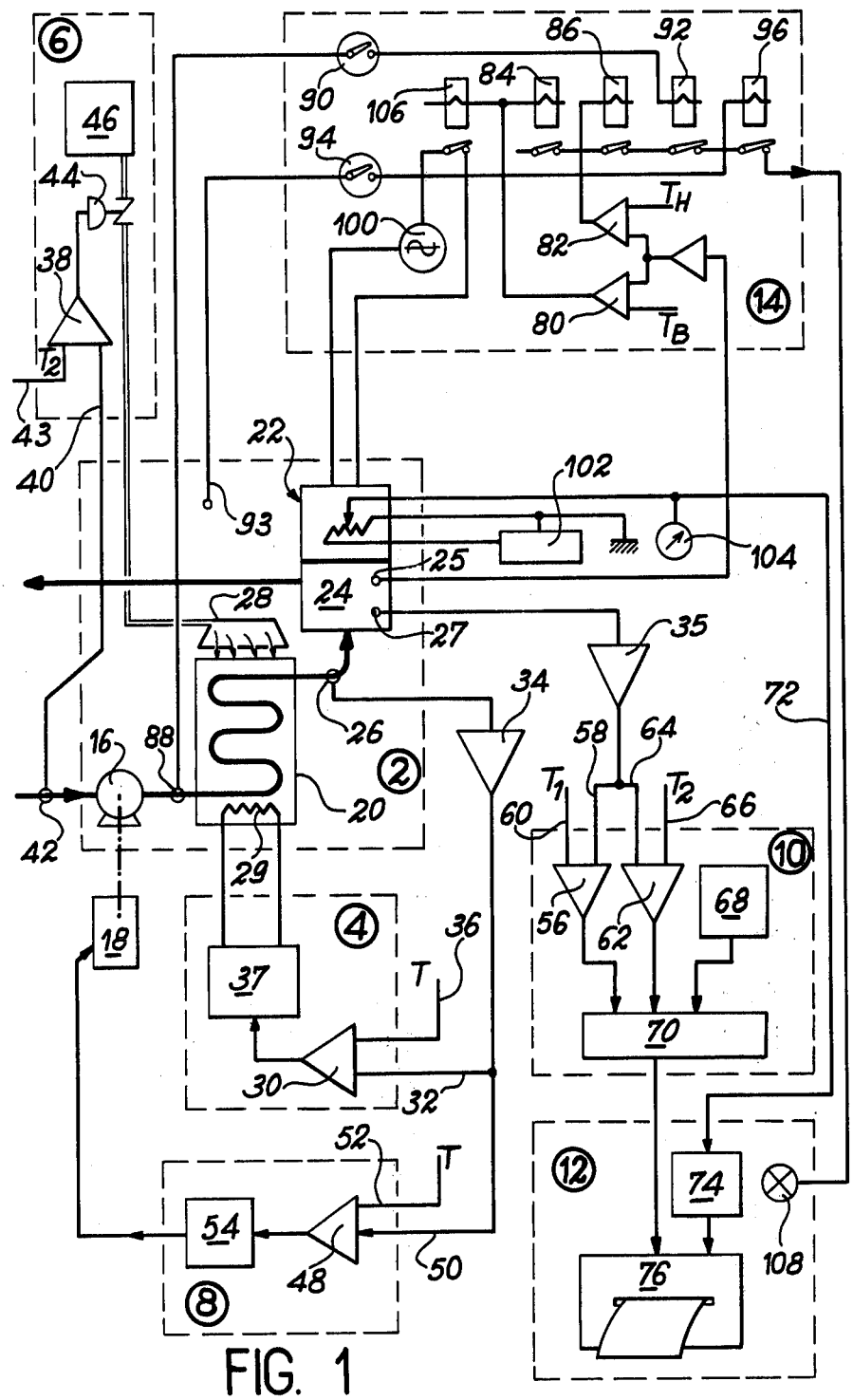
FIG. 1 is a general arrangement diagram of the instrument in accordance with the invention.

The instrument shown in the general diagram of FIG. 1 essentially comprises a measuring unit 2 in the form of a box, heat-regulating means 4, cooling means 6, flow-regulating means 8, a measurement validation circuit 10, devices 12 for displaying the result of the measurement and finally a safety element unit 14, all these means being described in detail hereinafter.

The measuring unit 2 is essentially constituted by an entraining pump 16 driven by a motor 18, a heat exchanger 20, a viscometer 22 comprising a measuring cell 24 in which is placed a temperature measuring probe 27; the heat exchanger 20 is associated with means 28 for blowing cold air and with a set of heating resistors 29.

Provision can be made at the outlet of the heat exchanger for a second temperature measuring probe 26. In an alternative embodiment, however, the probes 26 and 27 can be combined in a single probe unit.

The heat regulating means 4 of the heat exchanger essentially comprise a regulator 30, the lead 32 of which receives the signal delivered by the probe 26 and amplified by an amplifier 34 and the lead 36 of which receives a reference voltage corresponding for example to the mean temperature T of the range in which a measurement of viscosity is to be taken. The output of the regulator 30 is connected to means 37 for controlling the voltage supply to the heating resistors 29. The regulator 30 is a conventional circuit which permits of proportional, integral and derivative regulation, for example.

The means 6 for lowering the temperature by means of cooling air comprise a comparator 38, the input 40 of which receives the signal delivered by a second probe 42 placed upstream of the pump 16 and the input 43 of which receives a reference signal corresponding for example to the upper-limit temperature $T_2$ of the measurement range and an electrovalve 44 connected to an air supply 46.

The flow-regulating means 8 comprise a regulator 48, the lead 50 of which receives the signal delivered by the amplifier 34 and the lead 52 of which receives a reference signal corresponding to the index value T of the temperature within the range of $T_1$ to $T_2$ and a speed-changing device 54 which produces action on the motor 18.

The measurement validation circuit 10 comprises means for determining whether the temperature is comprised between a top value and a bottom value or not and means for preventing processing of the measurement when the temperature is not comprised between said top and bottom values. In the alternative embodiment which is illustrated, said circuit 10 comprises a first comparator 56, the lead 58 of which receives the signal delivered by an amplifier 35 which in turn receives the signal delivered by the probe 27 whilst the lead 60 receives a signal representing the lower-limit temperature $T_1$; a second comparator 62, the input 64 of which receives the signal delivered by the amplifier 35 and the input 66 of which receives a signal corresponding to the upper-limit temperature $T_2$; an oscillating circuit 68; a logical AND-gate 70 which is connected to the comparators 56 and 62 and to the oscillator 68 and controls the printer 76.

It is readily apparent that an analog gate could also be employed instead of the logical gate and would in such a case be connected to the output 72 of the viscometer.

The means 12 for displaying the result of the measurement comprise a digital voltmeter 74 connected to the viscometer through the lead 72 and a printer 76 controlled by the gate 70.

The safety means 14 essentially comprise comparators 80 and 82, one of the inputs of which receives the signal which may be amplified and is delivered by a temperature measuring probe 25 which is located within the measuring cell 24 in the same manner as the probe 27; the other input of said comparators receives reference signals corresponding to upper-limit and lower-limit threshold temperatures $T_H$ and $T_B$; the comparator 80 is connected to a safety relay 84 and the comparator 82 is connected to a safety relay 86; a bitumen pressure inlet 88 is provided at the outlet of the pump 16 and connected to a pressure gage (gauge) 90 which controls a safety relay 92; an air inlet 93 located within the unit 2; the actions 4, 8, 10 and 14 are grouped together within the unit 2 and this latter is connected to a pressure gage 94 which controls a relay 96. A general fault indicator lamp 108 located within the unit 12 is connected to the group of relays 84, 86, 92 and 96.

The complete assembly is completed by a source 100 for the supply of alternating-current to the viscometer 22, by a supply relay 106 and by a source 102 for the supply of current to the measuring signal transmitter; said measuring signal may be displayed on a voltmeter 104 if necessary.

The operation of the instrument described in the foregoing is as follows: the bitumen whose viscosity is to be measured is introduced into the measuring unit 2 by means of the pump 16 which injects it into the heat exchanger 20, the structural design of which will be more readily understood with reference to FIG. 3. The bitumen is then directed towards the viscometer 22 and passed from this latter into the measuring chamber 24. Measurement of viscosity is carried out in a conventional manner by the so-called Brookfield method and the result of the measurement appears on the lead 72 in the form of a voltage which is proportional to the viscosity.

In an alternative embodiment of the invention, a temperature measuring probe 26 is placed at the outlet of the heat exchanger 20. Said probe delivers a signal which serves to control the temperature regulating means in the manner which will now be described.

The signal delivered by the probe is first amplified by the amplifier 34, then directed towards the regulating means 4 and 8. The signal applied to the regulator 30 of the circuit 4 serves to determine whether the temperature of the bitumen is either lower or higher than the mean temperature T. In practice and as mentioned earlier, this value T is equal to 150° C. If the measured temperature is lower than T, the regulator 30 delivers a signal which produces action on the means 37 for controlling the supply of the resistors 29. In practice, said means 37 are constituted by a thyristor power module.

The signal delivered by the amplifier 34 which is also applied to the input of the regulator 48 of the flow-regulating means 8 serves to determine whether the measured temperature is lower or higher than an index value T equal to 150° C., for example. If the temperature of the bitumen is lower than the index value, the comparator 48 delivers a signal which produces action on the speed-changing device 54 in such a manner that the motor 18 is slowed-down and that the output of the pump decreases, with the result that said bitumen passes through the heat exchanger at a lower rate of flow and consequently undergoes a further temperature rise. Conversely, if the measured temperature is higher than the index temperature T, the comparator 48 delivers a signal of opposite polarity which initiates an increase in speed of the motor and consequently an acceleration of the pump output, thereby reducing the time of transit of the bitumen within the heat exchanger and reducing the bitumen outlet temperature.

The means 6 for reducing temperature by means of cooling air are carried into effect as soon as the comparator 38 indicates that the temperature of the bitumen admitted into the pump is higher than the limiting value $T_2$. To this end, said comparator 38 delivers a signal which initiates opening of the electrovalve 44 and consequently the flow of an airstream which is directed onto the wall of the flat heat exchanger by means of the device 28.

The two means 4 and 6 employed respectively for heating and cooling the wall of the heat exchanger are always present since they are conducive to opposite effects. In simplified alternative designs, however, the flow-regulating means 8 could be dispensed with. The flow-regulating means just mentioned can nevertheless be employed to advantage in combination with the two means 4 and 6. In this case, the temperature of the bitumen at the outlet of the flat heat exchanger depends on the one hand on the temperature of the wall and on the other hand on the flow rate of the bitumen. Two parameters are accordingly available for regulating said temperature.

In certain alternative embodiments, it is possible to combine continuous flow regulation with non-continuous heat regulation. In more precise terms, the temperature of the bitumen discharged from the heat exchanger can be varied within a range of approximately 30° C. solely by the effect of flow variation. Coarse regulation of the heating means or of the cooling means can accordingly be carried out so as to control abrupt variations in bitumen temperature of the order of 30° C. whilst fine regulation can then be carried out by the flow-regulating means.

The measurement validation circuit 10 operates in the following manner: the logical AND-gate 70 initiates recording of the result only if said gate receives pulses both from the comparators 56 and 62 and from the oscillator 68. If the bitumen temperature within the measuring cell 24 is located between the terminals $T_1$ and $T_2$, a signal is applied to the printer 76 at each pulse of the oscillator 68. The printer 76 therefore gives the values of viscosity only if the bitumen temperature is suitable. The digital voltmeter 74 receives the measuring signal continuously and gives the result of the measurement even if the temperature is outside the correct range.

The safety means 14 operate in a conventional manner. The relays employed can be associated with warning lamps which are intended to indicate the presence of a fault.

The measuring cell 24 is not illustrated in detail since it is of conventional type but nevertheless has a very small dead volume in order to increase the speed of measurement. The cell is usually designed in the form of a cone frustum within which a disc is rotatably mounted. In accordance with the invention, the bases of the cone frustum are brought as close as possible to the disc.

Figure 2:
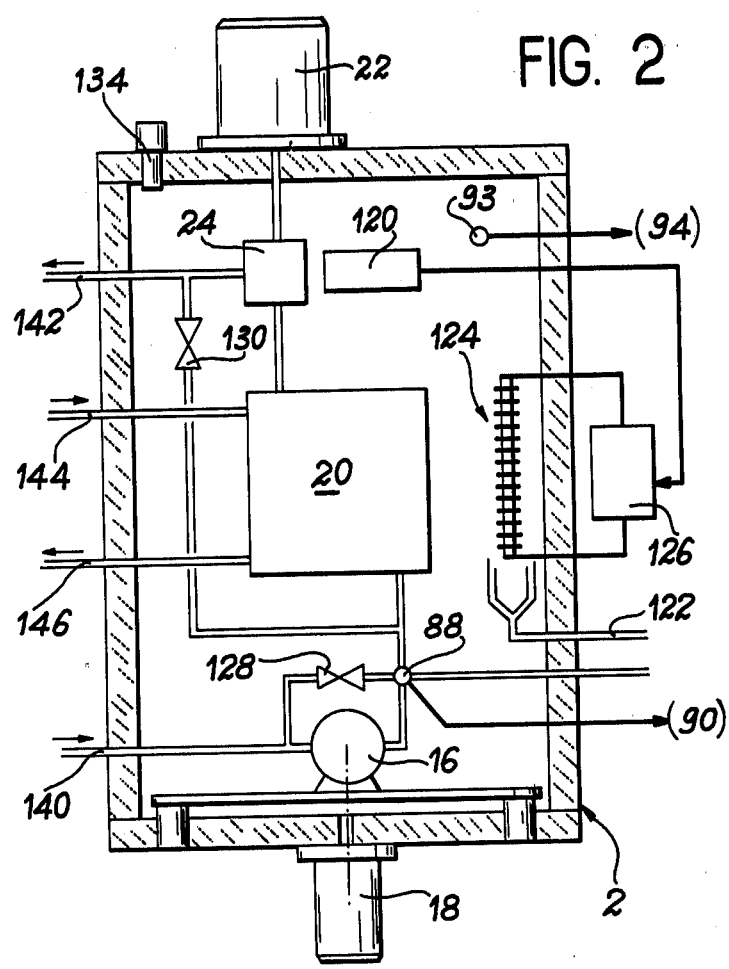
FIG. 2 is a diagram of the measuring unit.

FIG. 2 shows in greater detail the measuring unit 2 in the form of a box in which or around which are placed the means already mentioned in connection with FIG. 1, namely: the pump 16, the motor 18, the heat exchanger 20, the measuring cell 24, the viscometer 22 proper, the bitumen pressure inlet 88 and the air pressure inlet 93. This figure also shows means for pressurizing and thermostatically controlling the interior of the box 2. Said means are constituted by a pressurization air injection pipe 122 and by heating resistors 124 supplied from a voltage source 126 controlled by a thermostat 120 placed in proximity to the cell 24. Preferably, the temperature of the enclosure is equal to or slightly lower than 150° C.

There are also noted in this figure a valve 128, the opening of which permits of recycling of the bitumen through the pump 16 in the event of clogging of the circulation system, for example; a second control valve 130 which makes it possible to prevent flow through the heat exchanger and the measuring cell, a calibrated check-valve 134, pipes 140 and 142 respectively for the admission and discharge of bitumen and pipes 144 and 146 respectively for the admission and discharge of cooling air.

Figure 3:
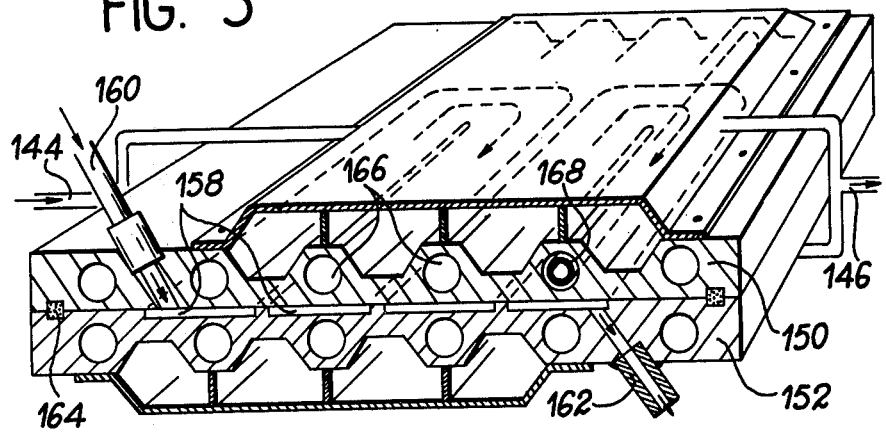
FIG. 3 is a general view of the heat exchanger.

FIG. 3 is a general transverse sectional view of the heat exchanger which is preferably employed in the instrument according to the invention in one embodiment which corresponds to a flat structure. The heat exchanger shown in this figure comprises two plate elements 150 and 152 having flat faces; the plate element 152 has a channel 158 which is machined in the flat face of said element and has the shape of a snaked coil. The depth of said channel is of the order of one millimeter. In the case of substances having poor thermal conductivity such as bitumen, it is an advantage to employ a channel having a depth of less than 2 mm. The bitumen is admitted through a pipe 160 and discharged through a pipe 162. A seal 164 is fitted between the two plate elements.

The wall constituted by the two plate elements is advantageously pierced by cylinders 166 in which are fitted heating resistors 168 of pencil-shaped design, for example. The cooling air admission and discharge pipes are again designated by the references 144 and 146.

The wall constituted by the two plate elements 150 and 152 should preferably have low thermal inertia; to this end, the plate elements can be of metal and especially of aluminum.

It will readily be understood that bitumen has been mentioned in the foregoing description only by way of explanation and that the instrument can operate with many other products such as heavy oil, fuels and the like.

What we claim is:

1. An instrument for continuous measurement of viscosity of bitumens in particular, of the type comprising a viscometer adapted to the product whose viscosity is to be measured, and an entraining pump for receiving and transferring said product to a heat exchanger constituted by a wall in which is formed a channel for the circulation of said product, said wall being brought to an adjustable temperature by suitable means, the output of said channel being connected to a viscometer, wherein the output of the entraining pump can be varied at will and wherein said instrument comprises in addition:

a probe for measuring the temperature of the product, said probe being placed within the viscometer at the point of measurement of viscosity, and regulating means for adjusting said temperature to an index value comprised between a lower-limit temperature $T_1$ and an upper-limit temperature $T_2$, said regulating means being adapted to produce action on the output of the pump and on the means for controlling the temperature of the heat-exchanger wall.

2. An instrument according to claim 1, wherein the heat-exchanger wall being fitted with heating resistors supplied from a voltage source, said means for regulating the temperature of the product comprise a first regulator which receives the measuring signal delivered by said probe aforesaid and a reference signal corresponding to the mean temperature T comprised between $T_1$ and $T_2$, said regulator being intended to deliver an order for initiating voltage supply to said heating resistors when said measuring signal is different from said reference signal.

3. An instrument according to claim 1 or claim 2, wherein the heat exchanger is provided with means for blowing cold air onto the wall and comprises a second temperature measuring probe placed upstream of the pump, said second probe being intended to deliver a measuring signal applied to a comparator which receives in addition a reference signal corresponding to the upper-limit temperature $T_2$ and which delivers a signal for initiating the action of the air blowing means when said measuring signal delivered by said second probe is higher than said reference signal.

4. An instrument according to claim 1 wherein said means for regulating the temperature of the product to an index value further comprise a second regulator which receives the signal delivered by one of said temperature-measuring probes and a reference signal corresponding to said index value, said regulator being intended to deliver a signal for initiating an increase or a decrease in output of the entraining pump according as the measuring signal is higher or lower than the index value.

5. An instrument according to claim 1, wherein said instrument further comprises at the output of the viscometer a measurement validation circuit comprising means for determining whether the temperature is comprised between a top value and a bottom value or not and means for preventing processing of the measurement when the temperature is not comprised between said top and bottom values.

6. An instrument according to claim 5, wherein said measurement validation circuit comprises a first comparator which receives a first reference value corresponding to the temperature $T_1$, a second comparator which receives a second reference value corresponding to the temperature $T_2$, a signal being emitted by each of the two comparators aforesaid when the temperature measuring signal is comprised between said two reference values; an oscillating circuit; a logical AND-gate connected to the output of said regulators at the output of the oscillator; a recording instrument which is controlled by the AND-gate and receives the signal emitted by the viscometer which may be converted to digital representation by a digital voltmeter, recording of the result of measurement of viscosity being thus prohibited when the temperature of the substance is not located within the range of $T_1$ to $T_2$ and permitted when said temperature lies within said range.

7. An instrument according to claim 1, wherein the heat exchanger is constituted by two plate elements having flat faces, at least one of the flat faces being provided with a channel having a depth comprised between a fraction of a millimeter and a few millimeters and having the shape of a snaked coil, said channel being intended to constitute a duct when the two plate elements are joined together by means of their flat faces, the product whose viscosity is to be measured being intended to flow through said duct.

8. An instrument according to claim 7, wherein the plate elements are pierced by cylindrical holes in which are fitted tubular heating resistors.

9. An instrument according to claim 7 or claim 8, wherein the plate elements are of metal and especially of aluminum.

10. An instrument according to claim 1, wherein a temperature measuring probe placed within the viscometer controls safety elements which are actuated if said temperature falls below a predetermined lower-limit temperature or rises above a predetermined upper-limit temperature.

11. An instrument according to claim 1, wherein a device for measuring the pressure of the product is placed at the pump outlet and connected to a safety device.

12. An instrument according to claim 1, wherein the measuring cell of the viscometer, the heat exchanger and the entraining pump are placed within an enclosure which is pressurized and thermostatically controlled at a temperature equal to or slightly lower than the index temperature at which a measurement of viscosity is to be performed.

* * * * *